US007910058B2

(12) United States Patent
Thomas et al.

(10) Patent No.: US 7,910,058 B2
(45) Date of Patent: Mar. 22, 2011

(54) CHROMOPHORE AND POLYMER CAPABLE OF DETECTING THE PRESENCE OF VARIOUS NEUROTOXINS AND METHOD OF USE

(75) Inventors: Johnson Thomas, Kingsport, TN (US); Philip Boudjouk, Fargo, ND (US)

(73) Assignee: NDSU—Research Foundation, Fargo, ND (US)

( * ) Notice: Subject to any disclaimer, the term of this patent is extended or adjusted under 35 U.S.C. 154(b) by 0 days.

(21) Appl. No.: 12/754,762

(22) Filed: Apr. 6, 2010

(65) Prior Publication Data
US 2011/0028721 A1 Feb. 3, 2011

Related U.S. Application Data

(62) Division of application No. 11/338,261, filed on Jan. 24, 2006, now Pat. No. 7,700,040.

(60) Provisional application No. 60/646,920, filed on Jan. 25, 2005.

(51) Int. Cl.
*G01N 21/76* (2006.01)

(52) U.S. Cl. ............ 422/52; 436/164; 436/172; 544/66; 544/235

(58) Field of Classification Search ........................ None
See application file for complete search history.

(56) References Cited

FOREIGN PATENT DOCUMENTS
WO 99/57222 A 11/1999

OTHER PUBLICATIONS

Teranishi et al. "Synthesis and enhanced chemiluminescence of new cyclomaltooligosaccharide (cyclodextrin)-bound 6-phenylimidazo[1,2-a]pyrazin-3(7H)-one". 1998. Carbohydrate Research. vol. 306, pp. 177-187.*
Diaz et al. "Phenol Derivatives as Enhancers and Inhibitors of Luminol-H2O2-Horseradish Peroxidase Chemiluminescence". 1998. J Biolumin Chemilumin. vol. 13. pp. 75-84.*
Dezotti, Marci W.C., Marco-A. De Paoli: "Poly(p-phenylene-co-2,5-pyrazine), A New Electrically Conductive Polymer", Synthetic Metals, vol. 29, 1989, pp. E41-E45, XP002385620.

* cited by examiner

*Primary Examiner* — Yelena G Gakh
*Assistant Examiner* — David Weisz
(74) *Attorney, Agent, or Firm* — Wendy K. Marsh

(57) ABSTRACT

Applicants have produced a chromophore and a polymer that are highly sensitive to the presence of various agents, including organophosphates, pesticides, neurotoxins, metal ions, some explosives, and biological toxins. The detection is accomplished by detecting a change in the fluorescence characteristics of the chromophore or polymer when in the presence of the agent to be detected. The chromophore and polymer may be incorporated into sensors of various types, and they are adaptable for potential field use in areas where detection of these types of agents is desired.

4 Claims, 4 Drawing Sheets

CHROMOPHORE AND POLYMER CAPABLE OF DETECTING THE PRESENCE OF VARIOUS NEUROTOXINS AND METHOD OF USE

CROSS-REFERENCE TO RELATED APPLICATION

This application claims priority to U.S. Provisional Patent Application Ser. No. 60/646,920 filed Jan. 25, 2005, which is incorporated by reference herein in its entirety.

This application is also a divisional of copending non-provisional application Ser. No. 11/338,261 filed Jan. 24, 2006, which is also incorporated by reference herein in its entirety.

GRANT REFERENCE

This research was federally funded under Defense Microelectronics Activity (DMA), Department of Defense, Contract No. 1-194003-04-2-0404. The government may have certain rights in this invention.

BACKGROUND OF THE INVENTION

A wide variety of toxins exist in nature and they can also be synthetically produced. They vary in their structural complexity, ranging from formic acid produced by ants to protein toxins produced by several bacteria. Neurotoxins are among the most poisonous and fastest acting toxins. They specifically target the nervous system of animals, including humans, by interfering with the transmission of nervous signals. Neurotoxins are generally more lethal than toxins produced by microbes, and can cause incapacitation or death of the affected individual within minutes of exposure. As a result, neurotoxins have been and will continue to be significant potential candidates for weaponization. Examples of weaponized neurotoxins include Tabun (GA), Sarin (GB), Soman (GD), Cyclosarin (GF), DFP, DMMP, and VX, among others.

Each of these listed neurotoxins, and others, are organophosphates. Their neurotoxic activity arises from their ability to inhibit the functionality of acetylcholine esterase (AChE). Under normal conditions, AChE catalyzes the hydrolysis of the neurotransmitter acetylcholine (ACh) to acetic acid and choline. This reaction allows cholinergic neurons to return to their resting state after activation. In the presence of organophosphates, however, AChE is inhibited and neurons are unable to return to their resting state. In low doses, this results in eye watering and excessive salivation, and in higher doses, individuals are afflicted with various conditions, including salivation, lacrimation, urination, defecation, gastro intestinal upset, and emesis. When dosage is high enough, exposure to these compounds can also result in death. It is these properties of organophosphates that make them particularly suited for use not only as pesticides, but also as potential chemical warfare agents.

Because of this potential use of organophosphates as weapons and the speed with which they attack the human body after exposure, there is a critical need for an efficient method to quickly and accurately detect these highly toxic compounds. While there have been several developments in the past decade for detection of organophosphates, including colorimetric detection methods, surface acoustic wave (SAW) devices, enzymatic assays, and interferometry, each of these has at least one disadvantage. The limitations of these existing methods include slow response time, lack of specificity, low sensitivity, operational complexity or non-portability. For example, two major approaches that have received extensive attention are immuno-based assays and DNA sequencing schemes. However, immuno-based assays are difficult to implement outside of the laboratory because of the instability of the antibodies involved and the necessity of including unstable reagents in the assay. And DNA sequencing techniques are time and instrument-intensive, so therefore they cannot meet the requirements for practical field use. Additionally, both approaches require extensive operator training to be properly implemented.

Another common approach to sensing the presence of organophosphates is to rely upon an immobilized AChE detector coupled to a transducer such as Ph electrodes, fiber optics, and piezo electric crystals. This approach, however, is hampered by several limitations. For example, immobilized enzymes are sensitive and detect a broad spectrum of AChE inhibitors. Because of this broad range sensitivity, they lack selectivity and are prone to false positive alerts, particularly when exposed to choline mimics.

In addition to detection of organophosphates, there is a need for any sensor to convert a detector's chemical, mechanical, or optical change into a measurable signal when the organophosphates are present. Many different types of sensors are known in the art. For example, chemical sensors often detect conductivity changes, amperometric changes, or potentiometric changes. Optical sensors detect changes in emission or absorption. Mechanical sensors can detect changes in mechanical properties or impedence. However, none of the known sensors are or can be linked to a detection sensitive material which provides both quickness of alert and accuracy of detection.

As can be seen from the foregoing, there is a need in the art for development of a way to quickly detect the presence of neurotoxins in such a way that can be utilized in non-laboratory applications, by minimally trained personnel, with a low incidence of false positive alerts.

It is therefore an object of the present invention to provide a neurotoxin-sensitive compound that can selectively detect various organophosphates agents over a range of concentrations and conditions.

A further object of this invention is to provide a compound for use in optoelectronic sensors to detect organophosphates agents.

It is another object of this invention to provide a polymer capable of use in optoelectric sensors for detection of organophosphates agents.

Another object of this invention is to provide a method for detecting organophosphate agents using lumiphoric compounds.

These and other objects of the present invention will become apparent from the description of the invention that follows.

BRIEF SUMMARY OF THE INVENTION

The invention described herein provides a practical method for using organic compounds and/or polymers to detect various bioactive and other types of agents that include halogen or methoxy groups, including organophosphates, neurotoxins, pesticides, metal ions, and combinations thereof. When the detection chromophore or polymer of the invention come in contact with the compound to be detected, the detection compound reacts with a compound to be detected, thereby changing the fluorescence properties of the detection compound. This change in fluorescence can then be measured and indicates the presence of the compound to be detected. The chromophore or polymer may be used in a variety of sensors, including optical electronic sensors, biosensors, and surface acoustic wave sensors for detection of the various organophosphate and other compounds that may be detected.

Transition metal complexes that are luminescent in room-temperature solution have been used in a variety of chemical and biochemical applications. Many of these applications require that the metal lumiphore be functionalized so that it can be appended to a molecule or macromolecule of interest or activated by chemical reaction. Such functionalized lumiphores have been used in electron-transfer studies, in the design of new biosensors, and in the formulation of emissive paints.

In the present invention, the binding capability of pyrazines and aminopyrazines to bind metals and other organic and biomolecules is utilized to synthesize new organic or polymeric materials whose fluorescence properties change when coming into contact with appropriate analytes.

This change in fluorescence characteristics can be used to produce a sensor to assist in the detection of these various compounds. These multi valiant interactions produce a distance-dependent fluorescence energy transfer, and can be used in a regent-free, highly sensitive, and specific sensing technology for detection of these toxins.

DETAILED DESCRIPTION OF THE PREFERRED EMBODIMENT

Figure 1:
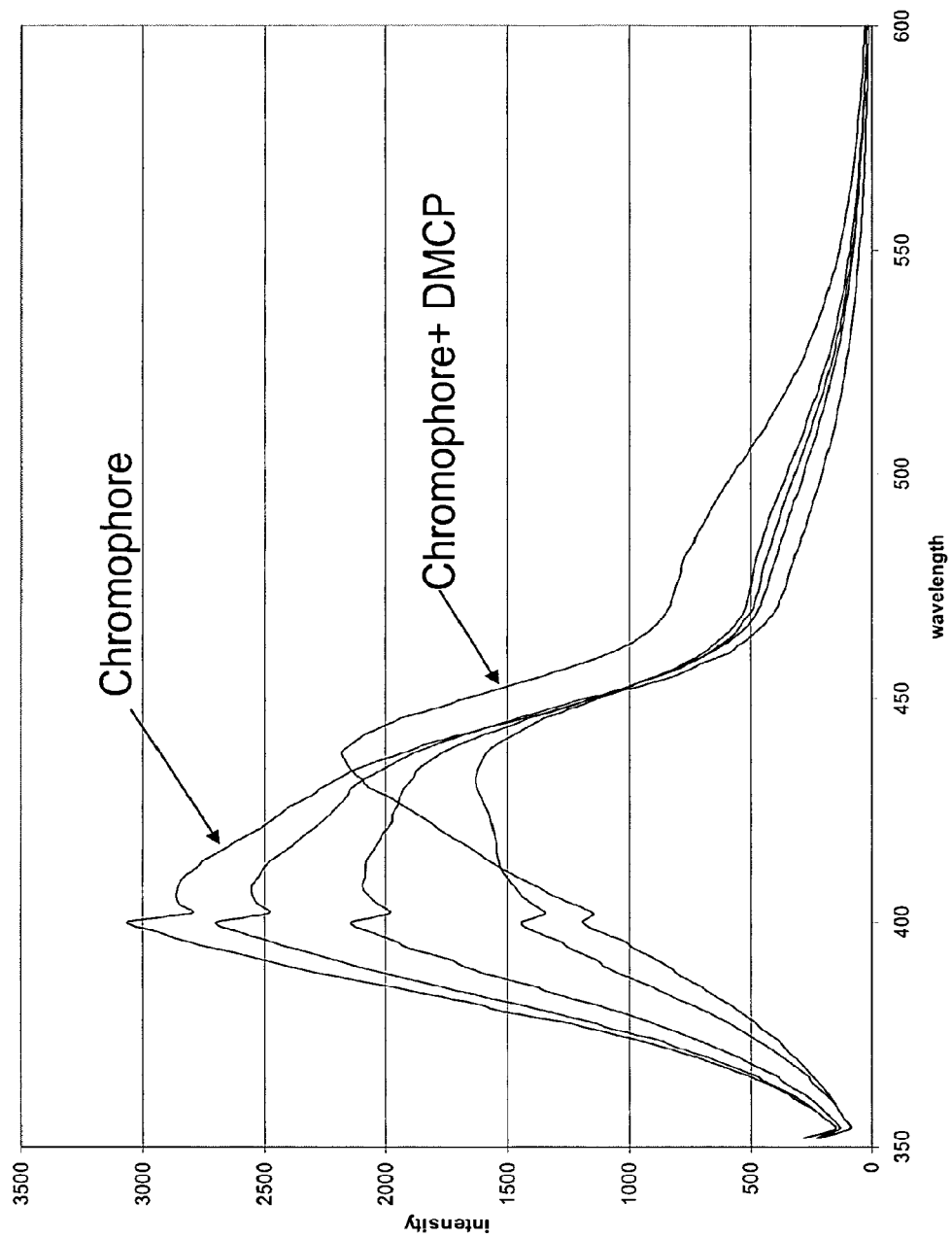
FIG. 1 is a graph showing the emission spectra of the chromophore of the present invention with dimethylchlorophosphonate (DMCP).
Figure 2:
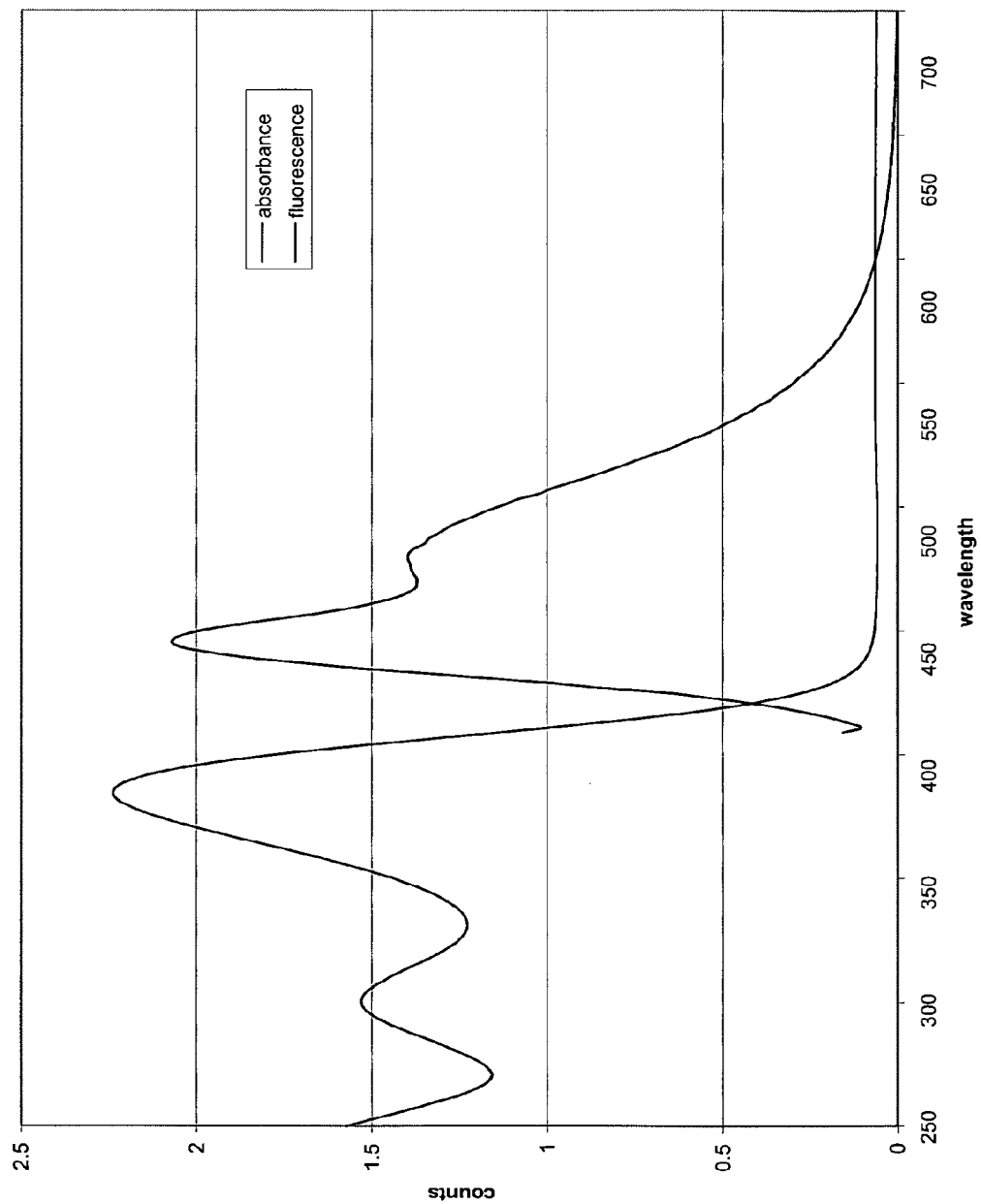
FIG. 2 illustrates the UV-Vis absorption and emission spectra of polyparaphenylene derivatives having amino pyrazine units as described in Example 1.

In its broadest sense, the invention comprises the use of a polymer or chromophore with luminescent properties that are either enabled (in the case of the chromophore) or disabled (in the case of the polymer) in the presence of a compound to be detected, and methods of using said polymer and/or chromophore to detect such compounds. In addition, the invention includes a method of producing the polymer and chromophore.

In a preferred embodiment, a polymer is produced that ceases to fluoresce when contacted with an organophosphate, neurotoxin, pesticide, metal ion, biological agent (or combinations thereof) or other types of compounds containing at least one halogenated group. Specific examples of halogenated neurotoxins include sarin, soman, GF, and DFP. While the present invention specifically refers to the use of detection agents for use in detecting neurotoxins, it is to be understood that the present invention is useful for detection of numerous compounds that contain one or more of the functional groups of interest.

In contrast to the polymer, the chromophore of the present invention fluoresces when contacted with an organophosphate, neurotoxin, pesticide, metal ion, biological and/or other types of compounds containing either a halogenated or methoxy-functional group.

The respective modes of detection of the polymer and the chromophore allow an effective dual means of detecting and identifying various compounds containing a halogenated and/or methoxy group. For instance, the chromophore can be used to generally detect the presence of a neurotoxin. Once a neurotoxin is detected, the polymer can be used to more specifically identify whether the neurotoxin is one containing a halogenated group. Alternatively, the polymer and chromophore can also be used individually to detect the presence of various halogenated and/or methoxylated neurotoxins.

The backbone of the polymer is generally made up of some combination of at least one of aminopyrazines, pyrazine, aminopyridine, or any amine containing an aromatic moiety; one or more of thiophene, pyridine, bipyridine, quinoline, isoquinoline, paraphenylene, hydroxyl paraphenylene, a phenyl group, or any hetero aromatic system. The backbone has a total number of between 1 and 100 units, with about 5-20 being preferred. The backbone preferably consists of pyrazine, aminopyridine, or aminopyrazine, with aminopyrazine being most preferred.

Preferred polymers of the present invention have the following general formula:

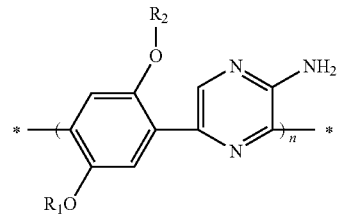

wherein $R_1$ is H, alkyl, cycloalkyl, benzyl, or any aromatic, heteroaromatic, or heterocyclic group; and n is an integer between 1 and 100; and $R_2$ is a $C_6$-$C_{15}$ alkyl chain. Again, n is preferably 5-20.

Most preferred polymers of this invention have the following general formula:

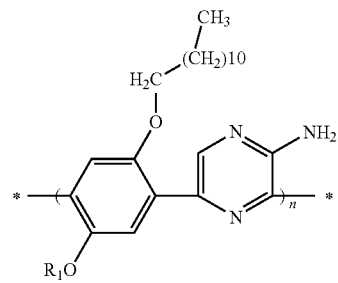

wherein $R_1$ is H, alkyl, cycloalkyl, benzyl, or any aromatic, heteroaromatic, or heterocyclic group; and n is an integer between 1 and 100, with 5-20 being preferred.

The chromophore of the present invention has the following general formula:

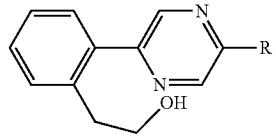

wherein R is H, $NH_2$, an aliphatic chain, or an aromatic group. The aliphatic chain is preferably $C_1$-$C_8$.

Preferred chromophores of the invention have one of the following formulas shown below:

[Chemical structure showing a chromophore with pyrazine-NH₂ group attached to a benzene ring system with OH group, and HO⁻]

[Chemical structure showing a chromophore with pyrazine group attached to benzene ring systems with OH group and methylphenyl group]

The chromophore and polymer are generally prepared by Suzuki coupling reactions. Such reactions are well known and understood in the art. In general, an organoborane is reacted with an organic halide in an organic solvent, such as tetrahydrofuran (THF) and ethers. This reaction preferably occurs in a nitrogen atmosphere with vigorous stirring at a temperature between 90-110° C. However, other temperatures, atmospheres, and reaction conditions are also appropriate, as would be understood to persons skilled in the art. The use of a palladium catalyst is also preferred. Once the reaction is complete, the organic phase is separated and the polymer precipitated therefrom. The precipitated polymer is then separated and dried using conventional means or can be retained in solution.

In the absence of neurotoxins, the polymer fluoresces in the presence of ultraviolet light. However, upon contact with the halogenated phosphate esters of neurotoxins, the polymer quenches the fluorescence of the neurotoxin, thereby facilitating its detection. This fluorescence quenching is the result of the NH₂ group of the conducting polymer hydrolyzing the halogenated phosphate ester and releasing acid which in turn oxidizes the polymer.

The detection of the organophosphate molecule by the change in fluorescence characteristics of the polymer occurs quite rapidly, typically in less than three seconds. Given this fast response time, the polymer is particularly suited for use in optoelectronic sensors.

In addition to the above-described polymer, a non-polymeric chromophore may also be used to detect the presence of the organophosphates and other biological agents already described above. The chromophore has the reverse fluorescence characteristics as the polymer, meaning that in the absence of organophosphate molecules, the chromophore does not fluoresce in the presence of ultraviolet light. The chromophore gains its fluorescence under ultraviolet light when a neurotoxin containing either a methoxy or halogenated group is present. The fluorescence is the result of the reaction of the OH of the chromophore with these functional groups.

The chromophore and polymer have different mechanisms of action to detect the presence of organophosphates or other compounds. Generally, the polymer hydrolyzes the halogenated phosphate ester of the organophosphate molecule and releases acid, which in turn oxidizes the polymer. This leads to formation of imine form of the polymer, which is not fluorescent after binding with the organophosphate. This imine form is depicted below:

[Chemical structure depicting the bound chromophore-organophosphate complex with Cl⁻HN, OCH₃ groups]

Figure 3:
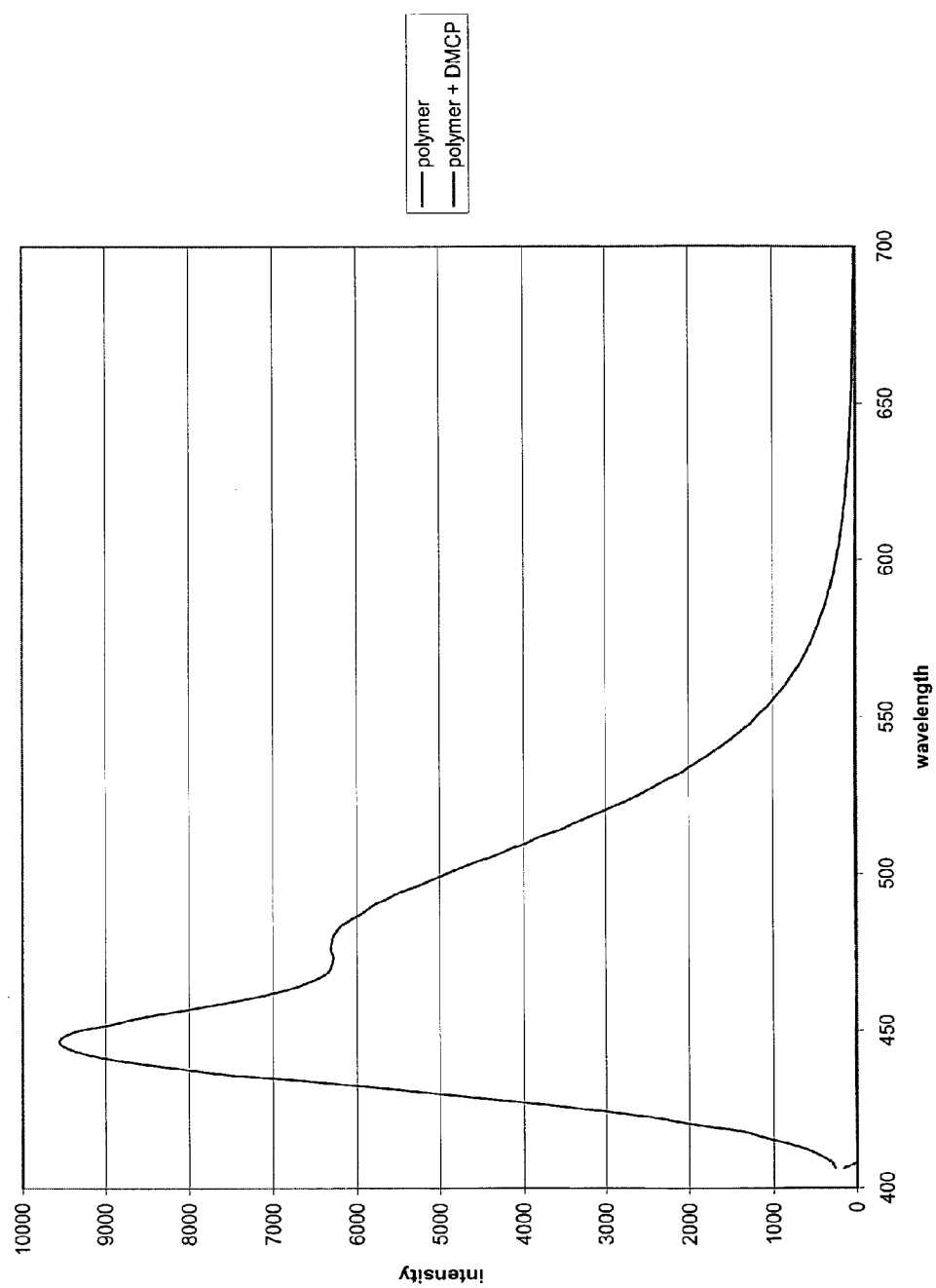
FIG. 3 illustrates the intensity of fluorescence of polymer and polymer+dimethylchlorophosphonate (DMCP).
Figure 4:
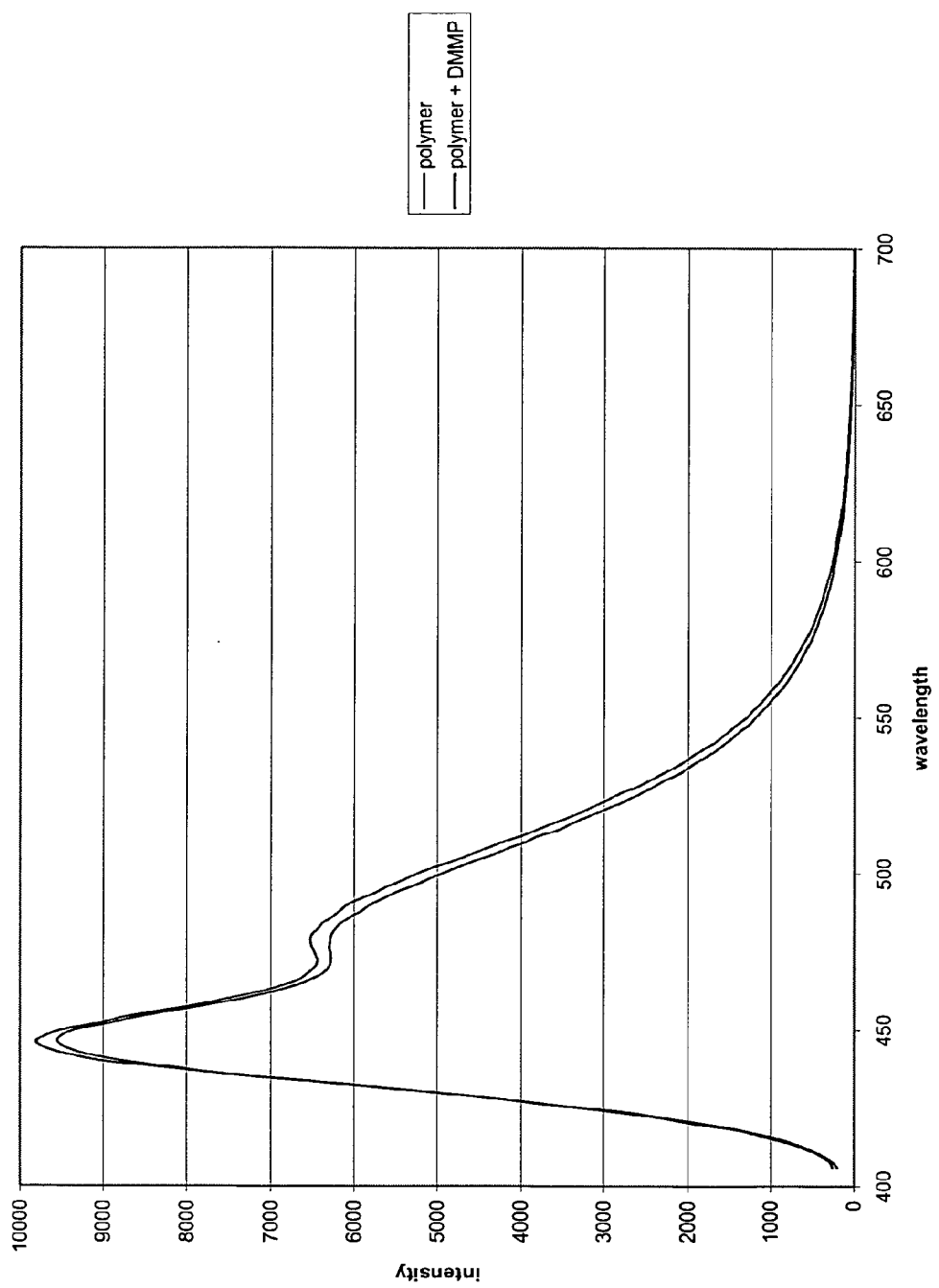
FIG. 4 illustrates the intensity of fluorescence of polymer and polymer+dimethyl methylphosphonate (DMMP).

Cyclic voltammetry shows that the polymer is oxidized in two steps, and the EIS measurement shows an increase in resistivity with oxidation. It is the increase in resistivity that explains the quenching of the fluorescence in response to the presence of organophosphate or other molecules capable of detection. FIG. 3 illustrates the intensity of fluorescence of unbound polymer compared to polymer bound to DMCP. FIG. 4 illustrates that polymer bound to dimethylmethylchlorophosphonate (a non-halogenated neurotoxin) has the same intensity of fluorescence as unbound polymer.

As noted, the chromophore detects the presence of organophosphates or other detectable molecules by interaction between the hydroxyl group and the methoxy or halogenated group of the neurotoxin molecule. This leads to a cyclization reaction which in turn produces the fluorescent molecule depicted below. The overall reaction is also shown:

[Chemical reaction scheme showing chromophore + DMCP → intermediate → final fluorescent product with A⁻ counterion]

where A⁻ is P O₂(OCH₃)₂⁻. FIG. 1 is a graph showing the emission spectra of the most preferred chromophore of the present invention (as shown above) with dimethylchlorophosphonate (DMCP).

Based on the above-described mechanisms of action, the chromophore and polymer described are able to detect a wide variety of compounds. The chromophore can detect any neurotoxin having a methoxy or halogenated group, and the polymer will detect halogenated neurotoxins specifically. Detectable compounds include organophosphates having the requisite halogen or methoxy group, such as sarin, cyclosarin, soman, tabun, diisopropylfluorophosphate, diethylchlorophosphate, VE, VG, VM, VX, metrifionate, pyridostigmine, and physostigmine; explosives such as plastic explosive or trinitrotoluene; and metal ions, such as iron, cobalt, nickel, copper, a transition metal ion, or a main group metal ion.

For years military force have used detection devices to identify these same materials but even today's best detection measures may require minutes for the user to receive an accurate alert to a potential hazard. Some detectors are quicker but they also provide more false alerts.

The polymer and chromophore of the present invention can accurately identify trace amounts of poisons or explosives having halogen and/or methoxy functional groups in seconds. These detection molecules can detect leaks in shipping containers of certain industrial chemicals, detect certain explosive compounds and detect an entire family of neurotoxins. In addition to giving advanced notice to the presence of hazards, the detection molecules can be used to authenticate the elimination of chemical agents or toxic substances during an investigation or clean-up operation.

The polymers of the present invention notify users via multiple feedback methods. They can be set to fluoresce in ultraviolet light yet remain clear in visible light. When in this mode, the fluorescence will quench as a toxic substance or explosive compound comes into contact it. Alternatively, the chromophore can provide no initial ultraviolet fluorescence, but fluoresces upon exposure to a toxic substance or explosive compounds.

The detection molecules of this invention also have the unique property of providing enough electrical activity upon coming into contact with a hazardous substance so that it can be integrated into many of today's existing electrical sensors.

Rapid alert notification to the presence of a fast acting neurotoxin is extremely important. Many chemical agents cause injury or death in less than a minute. Speed is also essential when multiple yet rapid and economical detections must be made (for example, hand screening of luggage). The detection molecules of the present invention provide accurate detection within 2 to 3 seconds of contact with a target substance as compared to minutes with similar technologies. These unique molecules are designed to detect trace amounts of:

the entire family of halogenated chemical compounds with very high selectivity;
the chemical warfare agents VX, GF, GB (Sarin), GD, (Soman) and GA (Tabun);
explosives (various plastic explosives and TNT); and
pesticides (organo-phosphonates like DFP and DMMP).

The detection molecules need only be applied in strengths ranging from parts-per-millions to part-per-billions. Further, under certain circumstances, the molecules can be reconditioned for repetitive use.

The detection molecules of the instant invention can be applied separately or together, and as an individual coating or mixed with other coatings. They can be sprayed or painted on to a surface, and can be applied to such simple materials a tape or cloth swabs, or applied to much more complex devices such as electronic sensors or electronic noses. Sensors incorporating either or both of the chromophore and/or polymer can be easily used in any location in which fast detection of neurotoxins is desired. Examples might include potential targets for terrorist attacks, such as subways, airports, aircraft, or government buildings. The basic performance and functionality of these molecules in detecting neurotoxins have been verified with fluorescence measurements, impedance testing and cyclic voltammetry.

In addition to being used to detect neurotoxins in the context of terrorism or chemical warfare, the polymer and chromophore described can also be used to detect the presence of organophosphates in the context of medical diagnosis or treatment monitoring. In fact, the polymer and chromophore may be used to detect neurotoxins in virtually any desired application.

The following examples are offered to illustrate but not limit the invention. Thus, they are presented with the understanding that various formulation modifications as well as method of delivery modifications may be made and still be within the spirit of the invention.

EXAMPLE 1

Preparation and Properties of a Preferred Polymer

A preferred polymer of the present invention was prepared by the following method:

a) 2,5-Dibromo-4-dodecyloxy phenol 2,5-Dibromohydroquinone 3 (40.2 g, 0.15 mol) was dissolved in a solution of sodium hydroxide (9.2 g, 0.23 mol) in 1.5 L of absolute ethanol at room temperature under nitrogen atmosphere. The reaction mixture was warmed to 50-60° C. with constant stirring. The dodecylbromide (36 ml, 0.15 mol) was added drop wise to the above reaction mixture at 60° C. After 10 h of stirring under nitrogen atmosphere, the reaction mixture was cooled and the precipitate formed was filtered and washed with methanol. This precipitate was identified as dialleylated-2,5-dibromohydroquinone as a side product. The filtrate was evaporated to remove the solvent. 2 L of distilled water was added to the residue and the mixture was acidified with 36% HCl, boiled gently for 1 h and cooled. The resulting precipitate was collected by filtration, washed with water and dried in vacuo. The crude product was purified by column chromatography using a mixture of solvents ($CH_2Cl_2$: hexanes, 4:6) to get the pure product in 60% yield.

$^1$H NMR, ($CDCl_3$, δ ppm): 7.25 (s, 1H), 6.97 (s, 1H), 5.16 (s, 1H), 3.92 (t, 2H), 1.62 (q, 2H), 1.4 (m, 18H); 0.88 (t, 3H).
$^1$H NMR ($CDCl_3$, δ ppm): 7.25 (s, 1H), 6.97 (s, 1H), 3.92 (t, 2H), 1.80 (q, 2H), 1.4 (m, 18H); 0.87 (t, 3H). $^{13}$C NMR ($CDCl_3$, δ ppm): 149.95, 146.64, 120.16, 116.49, 112.34, 108.26, 70.25, 31.81, 29.55, 29.47, 29.26, 29.20, 28.97, 25.82, 22.60, 14.04.

b) 2,5-Dibromo-1-benzylozy-4-dodecyloxy benzene

Benzyl bromide (3.8 ml, 0.031 mol) was added drop wise to a stirred solution of 2,5-dibromo-4-dodecyloxy phenol (a) (6.95 g, 0.015 mol) and anhydrous $K_2CO_3$ (3.28 g, 0.023 mol) in 700 ml of absolute ethanol at 40-50° C. The reaction mixture was stirred for 10 h at 50° C., progress of the reaction was monitored using TLC, cooled to RT and evaporated to remove the solvent. An equal volume of distilled water was added to the residue and the mixture was stirred for one hour at 0° C. The resulting precipitate was collected by filtration, washed with water, and dried in vacuum. Recrystallization was done in methanol to get 80% yield.

$^1$H NMR ($CDCl_3$, δ ppm): 7.46 (m, 5H), 7.21 (s, 1H), 7.15 (s, 1H), 5.11 (s, 2H), 3.99 (t, 2H), 1.85 (q, 2H), 1.32 (m, 18H), 0.95 (t, 3H). $^{13}$C NMR ($CDCl_3$, δ ppm): 150.51, 149.49, 136.16, 128.50, 128.10, 127.17, 119.32, 118.31, 111.53, 111.01, 71.99, 70.19, 31.83, 29.56, 25.84, 22.60, 14.02 c) 1-Benzyloxy-4-dodecylozyphenyl-2,5-bisboronic acid 1.6 M Solution of butyl lithium in hexanes (55 ml, 0.088 mol) was added slowly to a solution of dibromide b (11.57 g, 0.022 mol) in a mixture of solvents diethyl ether (150 ml) and THF (150 ml) under nitrogen atmosphere at −78° C. The solution was warmed to RT and cooled again to −78° C. Triisopropyl borate (51 ml) was added drop wise within 2 h. After complete addition, the mixture was warmed to RT and stirred overnight. Water was added and the mixture stirred for 24 h. The crystalline mass was recovered by filtration. The product was re crystallized from acetone in 80% yield.

$^1$H NMR (DMSO-d$_6$, δ ppm): 7.80 (s, 2H), 7.75 (s, 2H), 7.46 (m, 5H), 7.29 (s, 1H), 7.17 (s, 1H), 5.11 (s, 2H), 3.99 (t, 2H), 1.73 (q, 2H), 1.24 (m, 18H), 0.85 (t, J=6 Hz, 3H). $^{13}$C NMR (DMSO-d$_6$, δ PPM): 157.00, 156.22, 137.16, 128.38, 127.77, 127.52, 118.28, 117.70, 70.05, 68.30, 31.2, 28.89, 25.38, 22.00, 13.87.

d) 1-Benzyloxy-4-dodecyloxy phenyl-2,5-bis(trimethylene boronate)

Diboronic acid c (8.2 g, 0.018 mol) and trimethylene glycol (5.2 in], 0.072 mol) were added to toluene (150 ml) at RT. Then the reaction mixture was refluxed for 3 h. The solvent was removed by rotovap. The residue was dissolved in CHCl$_3$, dried over sodium sulfate and filtered. The solution was evaporated and the residue was re crystallized from hexanes. The recrystallized product was used without further purification for polymerization.

$^1$H NMR (CDCl$_3$, δ ppm): 7.35 (m, 5H), 5.05 (s, 2H), 4.16 (d, 8H), 3.85 (t, 3H), 2.02 (m, 4H), 1.57 (m, 2H), 1.27 (m, 18H), 0.88 (t, 3H). $^{13}$C NMR (CDCl$_3$, δ ppm): 157.73, 156.92, 138.28, 128.06, 127.00, 120.42, 119.79, 71.70, 69.70, 61.91, 31.81, 29.55, 27.22, 25.98, 22.57, 14.01.

e) 2-Amino-3,5-dibromopyrazine

Under absence of light and at 0° C., N-bromosuccinimide (15.68 g, 88.1 mmol) was added to a solution of 2-aminopyrazine (4.19 g, 44.06 mmol) in dry dichloromethane (250 ml). The mixture was stirred for 20 h at 4° C. and then washed with four 40 ml portions of a saturated sodium carbonate solution in water. The organic layer was dried (MgSO$_4$) and evaporated under reduced pressure, affording the title compound as 12.8 g of a light brown solid. Column chromatography, using silica and a dichloromethane/ethyl acetate (3/1) mixture as the eluent, yielded pure 2-amino-3,5-dibromopyrazine as 5.00 g (65%) of a light yellow solid.

1H-NMR (CDCl$_3$, 400 Mhz): 8.09 (s, I H), 4.95 (211, NH) ppm. 13C-NMR (CDCl3): 153.5 (C-2), 144.3, 131.9, 126.8 ppm f) Synthesis of Poly(p-phenylene)-co-amino pyrazine polymer

Diboronic ester d (0.97 g, 0.186 mmol) and dibromo aminopyrazine e (0.458, 0.186 mmol) were added to dry THF (10 ml) under nitrogen atmosphere. 2M Na$_2$CO$_3$ (15 ml) was added to this followed by palladium catalyst tetrakis(triphenylphosphino)palladium (1.5 mol % with respect to monomer d). The mixture was then heated to 100° C. for 72 h in a flask with vigorous stirring. After the reaction, the organic phase was separated and the polymer precipitated from hexane. The precipitated polymer was separated and dried to yield 0.5 g of polymer (Yield=60%). GPC analysis showed a number average molecular weight of 5300.

This leads to production of the following preferred polymer:

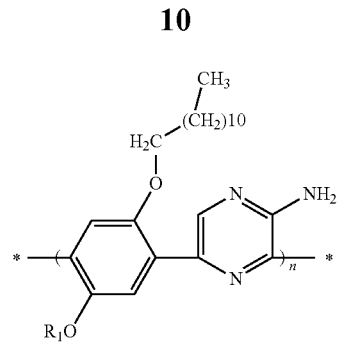

EXAMPLE 2

Preparation of a Preferred Chromophore a) Benzyl bromide (7 ml, 0.05 mol) was added drop wise to a stirred solution 2 bromo phenethyl alcohol (10 g, 0.0496 mol) and anhydrous NaH (2.28 g, 0.05 mol) in 100 ml of dry THF at 40-50° C. The reaction mixture was stirred for 10 h at 50° C., progress of the reaction was monitored using TLC, cooled to RT and evaporated to remove the solvent. An equal volume of distilled water was added to the residue and the mixture was stirred for one hour at ambient. The organic layer was separated, dried and evaporated. To the resulting liquid 100 ml of 5% ethanolic solution of NaOH was added and refluxed for 3 hr. The resulting solution was evaporated and extracted with ether to give the benzyl protected phenethyl alcohol as a clear liquid at 80% yield.

1H-NMR (CDCl$_3$, 400 Mhz): 7.5 (d, 1H), 7.3 (m, 7H), 7.08 (d, 1H), 4.53 (s, 2H), 3.7 (t, 2H), 3.07 (t, 2H) ppm. 13C-NMR (CDCl3, 100 Mhz): 138.43, 132.96, 131.37, 129.01, 128.58, 128.20, 127.78, 127.76, 127.57, 124.87, 73.12, 69.56, 36.71 ppm.

b) 1.6 M Solution of butyl lithium in hexanes (66 ml, 0.1 mol) was added slowly to a solution of 2-bromo O-benzyl phenethyl alcohol (9.7 g, 0.033 mol) in a mixture of solvents diethyl ether (150 nil) and THF (150 ml) under nitrogen atmosphere at −78° C. The solution was warmed to RT and recooled to −78° C. Triisopropylborate (23.1 ml) was added drop wise within 2 h. After complete addition, the mixture was warmed to RT and stirred overnight. Water was added and the mixture stirred for 24 h. The organic phase was separated and column chromatography of the resulting viscous liquid using dichloromethane as the eluent gave the boronic acid as white crystalline solid in 65% yield.

1H-NMR (CDCl3, 400 Mhz): 7.8 (d, 1H), 7.4 (t, 2H), 7.3 (m, 4H), 7.2 (d, 1H), 7.1 (d, 1H) 4.53 (s, 2H), 3.75 (t, 2H), 3.07 (t, 2H) ppm. 13C-NMR (CDCl3, 100 Mhz): 143.78, 136.79, 134.15, 130.44, 129.32, 128.69, 128.20, 127.95, 126.13, 73.74, 72.47, 36.89 ppm.

c) Under absence of light and at 0° C., N-bromosuccinimide (7.84 g, 44.05 mmol) was added to a solution of 2-aminopyrazine (4.19 g, 44.06 mmol) in dry dichloromethane (250 ml). The mixture was stirred for 20 h at 4° C. and then washed with four 40 ml portions of a saturated sodium carbonate solution in water. The organic layer was dried (MgSO$_4$) and evaporated under reduced pressure, affording the title compound as 5.90 g of a light brown solid. Column chromatography, using silica and a dichloromethane/ethyl acetate (3/1) mixture as the eluent, yielded pure 2-bromo-5-aminopyrazine as 5.00 g (65%) of a light yellow solid.

1H-NMR (CDCl3, 400 Mhz): 8.09 (s, 1H, H-6), 7.77 (s, 1H, H-3), 4.65 (bs, 2H, NH) ppm. 13C-NMR (CDCl3, 100 Mhz): 153.5 (C-2), 144.3 (C-6), 131.9 (C-3), 126.8 (C-5) ppm.

d) The boronic acid (0.8 g, 3.26 mmol) and bromo pyrazine (0.56 g, 3.26 mmol) were added to dry toluene (20 ml) under nitrogen atmosphere. 2M $Na_2CO_3$ (15 ml) was added to this followed by palladium catalyst tetrakis (triphenylphosphino) palladium (1.5 mol % with respect to boronic acid). The mixture was then heated to 80° C. for 48 h with vigorous stirring. The reaction mixture was evaporated, washed with water and the organic phase was separated. Column chromatography of the compound using 1:1 Ethyl Acetate/Hexane mixture gave 60% of the required product.

1H-NMR (CDCl3, 400 Mhz): 8.15 (s, 1H), 8.01 (s, 1H), 7.25 (m, 9H), 4.58 (s, 2H, —NH), 4.6 (s, 2H), 3.6 (t, 2H), 3.01 (t, 2H) ppm. 13C-NMR (CDCl3, 100 Mhz): 152.95, 145.20, 141.98, 138.65, 137.71, 137.33, 131.28, 130.85, 130.10, 128.56, 127.80, 127.71, 126.73, 72.97, 71.20, 33.64.

e) The O-benzyl protected compound was dissolved in a mixture of dry THF (50 ml) and absolute ethanol (50 ml) at RT. 10% Pd/C (3 g) was added to the above solution. The mixture was flushed with nitrogen gas three times. Two to three drops of conc. HCl was added to enhance the debenzylation. The reaction was carried out at RT under positive pressure of hydrogen for 24 h with constant stirring. The reaction mixture was filtered through celite powder and the precipitate was washed with absolute ethanol. The filtrate was evaporated and dried in vacuum to yield the desired Chromophore at 50% yield.

IH-NMR (CDCl3, 400 Mhz): 8.19 (s, 1H), 8.06 (s, 1H), 7.30 (m, 4H), 4.78 (s, 2H, —NH), 3.6 (t, 2H), 3.05 (t, 2H) ppm. 13C-NMR (CDCl3, 100 Mhz): 153.08, 145.20, 141.98, 138.65, 137.71, 131.28, 130.85, 128.56, 126.73, 64.26, 33.64.

This yields the preferred chromophore below:

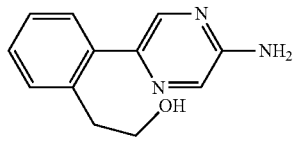

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A chromophore having the following structure:

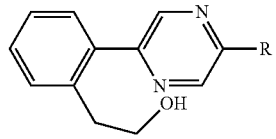

wherein R is H, $NH_2$, an aliphatic chain, or an amino group.

2. A sensor for detecting a harmful compound comprising a chromophore, said chromophore having the following structure:

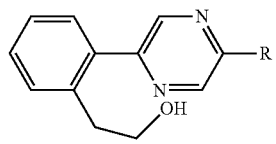

wherein R is $NH_2$ or an amino group; said harmful compound having a substituent selected from the group consisting of halogenated chemical compounds, a chemical warfare agent selected from the group consisting of VX, GF, GV (Sarin), GD (Soman), and GA (Tabun), explosives, and organo-phosphonate pesticides.

3. The sensor of claim 2 selected from the group consisting of optoelectronic sensor, biosensor, and surface acoustic wave sensor.

4. A chromophore having one of the following general formulas:

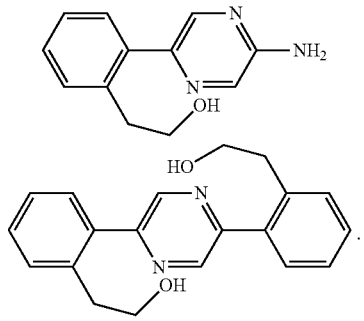

* * * * *